US006908769B2

(12) United States Patent
Belik et al.

(10) Patent No.: US 6,908,769 B2
(45) Date of Patent: Jun. 21, 2005

(54) DYE PAIR FOR FLUORESCENCE RESONANCE ENERGY TRANSFER (FRET) MEASUREMENTS

(75) Inventors: Daniel Belik, Penzberg (DE); Hans-Peter Josel, Weilheim (DE); Rupert Herrmann, Weilheim (DE); Bernard Koenig, Berg (DE); Francis Mueller, Basel (CH)

(73) Assignee: Roche Diagnostics GmbH, Penzberg (DE)

( * ) Notice: Subject to any disclaimer, the term of this patent is extended or adjusted under 35 U.S.C. 154(b) by 0 days.

(21) Appl. No.: 10/432,132

(22) PCT Filed: Nov. 14, 2001

(86) PCT No.: PCT/EP01/13152

§ 371 (c)(1),
(2), (4) Date: Oct. 24, 2003

(87) PCT Pub. No.: WO02/41001

PCT Pub. Date: May 23, 2002

(65) Prior Publication Data

US 2004/0076979 A1 Apr. 22, 2004

(30) Foreign Application Priority Data

Nov. 16, 2000 (EP) ............................................. 00124995

(51) Int. Cl.⁷ .............................................. G01N 21/64
(52) U.S. Cl. ........................ 436/172; 436/537; 436/84; 436/94; 422/61
(58) Field of Search ........................... 250/458.1, 459.1; 436/172, 84, 86, 87, 94, 166, 536, 537; 422/61

(56) References Cited

U.S. PATENT DOCUMENTS

| 4,822,733 A | * | 4/1989 | Morrison | 435/6 |
| 5,246,867 A | * | 9/1993 | Lakowicz et al. | 436/95 |
| 5,656,433 A | * | 8/1997 | Selvin et al. | 435/6 |
| 5,998,146 A | * | 12/1999 | Latva et al. | 435/6 |
| 6,245,514 B1 | * | 6/2001 | Wittwer | 435/6 |
| 6,444,476 B1 | * | 9/2002 | Morgan | 436/172 |

FOREIGN PATENT DOCUMENTS

| EP | 0 076 695 A1 | 6/1981 |
| WO | WO 93/10189 | 5/1993 |
| WO | WO 98/43072 | 10/1998 |
| WO | WO 99/51986 | 4/1999 |
| WO | WO 00/47693 | 8/2000 |

OTHER PUBLICATIONS

International Search Report (no date).

Blomberg et al. Clinical Chemistry 45 (1999) 855 ff (no month).

Blomberg et al. Clinical Chemistry 45 (1999) 855 ff.

French et al., SPIE BiOS in Proc. SPIE v 3259 (1998) 209–218.

Mujumdar et al., Bioconjugate Chem. 7, 1996, 356–362.

Youn et al. Analytical Biochemistry 232 (1995) 24–30.

* cited by examiner

*Primary Examiner*—Jeffrey R. Snay
(74) *Attorney, Agent, or Firm*—McDonnell Boehnen Hulbert & Berghoff LLP

(57) ABSTRACT

The present invention concerns new fluorescent dye systems especially for fluorescence resonance energy transfer determinations for example combined with the time-resolved measurement of the resulting fluorescence. The invention also concerns the use of these dyes to label biomolecules and for the homogeneous determination of interactions between biomolecules, for example for detecting an analyte.

12 Claims, 1 Drawing Sheet

Figure 1: Diagram of the measuring device
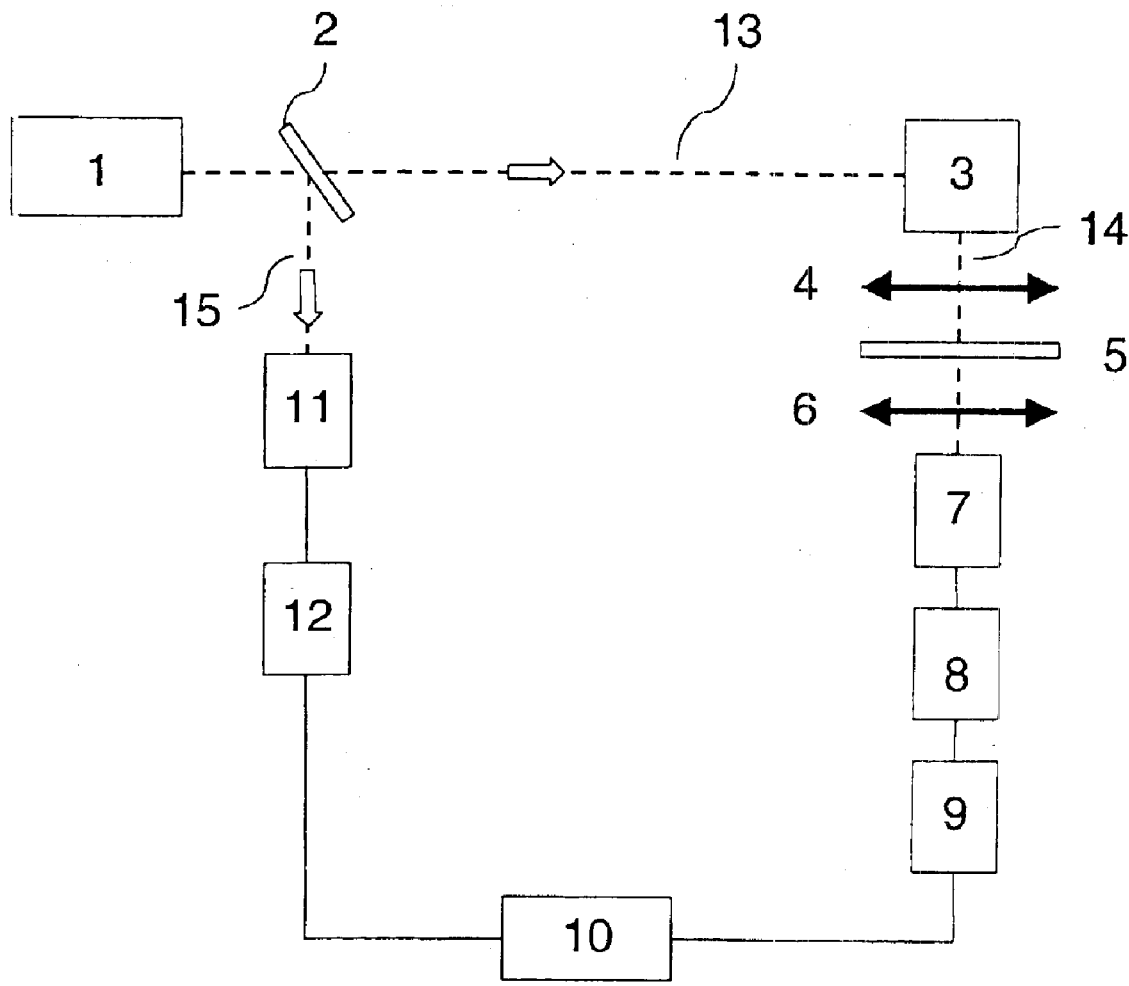
1. light source
2. quartz plate
3. sample
4. collecting lens
5. optical filter
6. focussing lens
7. photomultiplier
8. amplifier
9. discriminator
10. counter
11. photodiode
12. gate switch
13. excitation light pulse
14. fluorescence light
15. light pulse for actuating
    the gate switch (trigger)

SEQUENCE LISTING

<160> NUMBER OF SEQ ID NOS: 1

<210> SEQ ID NO 1
<211> LENGTH: 9
<212> TYPE: PRT
<213> ORGANISM: Artificial
<220> FEATURE:
<223> OTHER INFORMATION: HA peptide

<400> SEQUENCE: 1

Thr Pro Thr Asp Val Pro Asp Thr Ala
1               5

DYE PAIR FOR FLUORESCENCE RESONANCE ENERGY TRANSFER (FRET) MEASUREMENTS

The present invention concerns new fluorescent dye systems especially for fluorescence resonance energy transfer determinations for example combined with the time-resolved measurement of the resulting fluorescence. The invention also concerns the use of these dyes to label biomolecules and for the homogeneous determination of interactions between biomolecules, for example in the detection of an analyte.

Binding partners that can specifically bind to the biomolecule that is to be detected or examined are very often used to determine biomolecules. A basic differentiation is made between heterogeneous and so-called homogeneous assays, the latter being characterized in that one or more washing steps are necessary to carry out the test.

In so-called heterogeneous assays at least one biomolecule is provided with a marker group. The concentration of the analyte molecule to be examined is ultimately determined by measuring this marker group. Of course this determination is only of practical use when the bound and unbound labelled binding partners have been separated by means of a suitable washing step before carrying out the measurement.

In conventional homogeneous assays the test conditions are selected such that measurable signal changes due to turbidity effects or scattered light effects which depend on the concentration of the analyte molecule that is present are generated. Particulate carrier materials are often used to amplify the generated signals in such assays.

Only in recent years has it become possible to carry out homogeneous determinations i.e. determinations that do not necessarily require an intermediate washing step, even when using marker groups. Further developments in the field of homogeneous immunoassays are all based on the interaction of at least two molecules which only occurs when these molecules are in direct proximity to one another. Homogeneous assays have become well-known that are based on the principles of "cloned enzyme donor immunoassays"= CEDIA (Microgenics Inc. USA), fluorescence polarization= FPIA (Syva Co. USA) or scintillation proximity assays (Amersham UK). However, special mention is made here of those methods that are based on the principle of fluorescence resonance energy transfer (FRET). Always at least two dye molecules are required for fluorescence energy transfer. A first dye which acts as an energy donor and a second dye which acts as an energy acceptor. The energy transfer between the donor and acceptor occurs non radiatively i.e. without emitting radiation.

The efficiency of FRET is very dependent on the distance between the donor and acceptor dye. FRET only occurs efficiently when the donor and acceptor are very close together.

Usually the donor molecule as well as the acceptor molecule are each bound to one partner of a bioaffine binding pair. If the carrier biomolecules interact and associate for example to form an antigen-antibody complex, the donor and acceptor molecule are also then in close proximity and FRET is possible.

The energy acceptors can either be selected such that they suppress the energy released by the donor which are referred to as quenchers or the fluorescence resonance energy acceptors can themselves release fluorescent energy i.e. they fluoresce, these are referred to as fluorophore groups or briefly as fluorophores. It is known from the prior art that metallic complexes are suitable as fluorescence energy donors as well as fluorescence energy acceptors.

As mentioned above fluorophore groups are also known as acceptors in FRET systems. In particular dyes from the group of allophycocyanins (APCs) are used as such fluorophores. A high quantum yield and very good absorbance properties are among some of the known properties of APCs (e.g. EP 076 695).

However, phycobiliproteins have disadvantages and thus for example due to the high molecular weight of more than 100,000 Da it is not possible to selectively couple them to a biomolecule i.e. via a predetermined position in the APC molecule. This coupling is usually chemical and hence statistical, or the binding is indirect using binding systems such as the streptavidin/biotin system known to a person skilled in the art. Also the sensitivity i.e. the lower limit of detection of these systems appears to be in need of improvement for example when detecting analyte molecules in low concentrations.

Commercial systems are available from Wallac, Oy, Turku, Finland and Packard Instrument Company, Meriden, USA, which use lanthanide chelates as the donor label and dyes from the phycobiliprotein class e.g. allophycocyanin as the acceptor label. The lanthanide chelates have a luminescence lifetime in a range up to several milliseconds i.e. the acceptor emission can be observed for a corresponding length of time. Hence the energy released by lanthanide chelates is usually measured in a time window between 400–600 microseconds. This also inevitably means that there are also relatively long dead times. The stability of the lanthanide chelates is reduced under certain test conditions; thus for example a re-chelation can occur when complexing agents such as EDTA (ethylene-di-amino-tetra-acetic acid) are added.

U.S. Pat. No. 5,998,146 describes the use of lanthanide chelate complexes in particular of europium and terbium complexes combined with fluorophores or quenchers. It also underscores the advantageous properties of the long-lived lanthanide chelate complexes.

Blomberg et al., Clinical Chemistry 45(6) (1999) 855 ff describe the use of europium or terbium complexes as donors and a rhodamine dye as an acceptor in new FRET pairs. The sensitivity of the detection of βhCG (β subunit of human chorionic gonadotrophin) is stated as 0.43 $\mu$g/L. Thus the FRET assays based on europium or terbium chelate complexes do not lead to a major improvement with regard to the sensitivity of the assays.

The use of ruthenium complexes for time-resolved fluorescent measurement is described for example in EP-A2-439 036 where lumazine is used as the energy donor and a ruthenium complex is used as the energy acceptor.

Joun et al., Analytical Biochemistry 232 (1995) 24–30 use fluorescent ruthenium complexes as energy donors for homogeneous determinations based on the FRET principle. The dye well-known under the trivial name "reactive blue" is used as the resonance energy acceptor. Reactive blue suppresses the fluorescence emitted by the ruthenium complex and hence the quantification is based on the suppressed fluorescence signal which was originally emitted by the ruthenium complex.

WO 00/47693 also describes the use of ruthenium chelate complexes as fluorescence energy donors in combination with quenchers. The ruthenium complex known under the trivial name "Fair Oaks Red™" was used as the energy donor. This dye was coupled to an antibody to human serum albumin. The antigen human serum albumin was labelled with a non-luminescent dye known as "light green yellowish". As with Joun et al., (see above) the analyte concentration (human serum albumin) was ultimately determined from the extent of signal suppression.

For the assay of biomolecules it is in very many cases also necessary to detect small quantities of the analyte molecule to be examined. The term lower limit of detection is often used to characterize the sensitivity of a measuring system. The lower this detection limit the more sensitive is the test system.

However, there is still considerable potential for improvement with regard to the simplicity of coupling FRET dyes to biomolecules and above all with regard to the sensitivity of tests that are based on the FRET principle. More sensitive homogeneous test procedures based on FRET measurements would have a broader and more diverse practical use and would therefore be very desirable.

Hence the object of the present invention was to search for and optionally to describe new FRET pairs which can overcome the known disadvantages of the prior art e.g. with regard to the lower limit of detection.

Surprisingly it was found that metallic chelate complexes based on metal ions of groups VII and VIII of the transition elements can be used to great advantage as energy donors in combination with low-molecular fluorophores as energy acceptors for example in sensitive methods for determining the interaction between biomolecules based on the FRET principle.

BRIEF DESCRIPTION OF THE INVENTION

The invention concerns methods for determining the interaction between biomolecules labelled with a donor or acceptor based on the principle of fluorescence energy transfer and measurement of the resulting fluorescence which are characterized in that metallic chelate complexes based on metal ions of groups VII and VIII of the transition elements are used as energy donors in combination with low molecular fluorophores having a molecular weight between 300 Da and 3000 Da as energy acceptors.

It was surprisingly found that low molecular fluorophores in particular from the dye classes rhodamines, xanthenes, cyanins and oxazines are excellently suitable for FRET measurements especially in combination with metallic chelate complexes based on metal ions of groups VII and VIII of the transition elements in particular ruthenium chelate donors, to construct improved FRET assays.

The FRET pairs according to the invention are especially suitable for the time-resolved measurement of the resulting energy (TR-FRET).

The dye combinations according to the invention are also suitable for methods for determining the interaction between biomolecules labelled with a donor or acceptor which are based on the principle of fluorescence modulation.

The new FRET pairs can now be used in a very advantageous manner to examine interactions of biomolecules especially when the biomolecules labelled with the FRET partners are firstly in very close spatial proximity and are further apart after interaction or conversely when they can be brought very close to one another for example by forming a complex between the partners of a bioaffine binding pair.

The invention improves and extends the possibilities for detecting numerous analyte molecules especially in so-called homogeneous test procedures and therefore also encompasses test kits for detecting an analyte in a sample which contain at least one biomolecule labelled with a metal chelate complex based on metal ions of groups VII and VIII of the transition elements, especially a biomolecule labelled with the ruthenium chelate complex, and a biomolecule labelled with a low molecular fluorophore acceptor.

DETAILED DESCRIPTION OF THE INVENTION

The invention essentially concerns methods for determining the interaction between biomolecules labelled with a donor or acceptor based on the principle of fluorescence energy transfer and measurement of the resulting fluorescence which are characterized in that metallic chelate complexes based on metal ions of groups VII and VIII of the transition elements are used as energy donors in combination with low molecular fluorophores having a molecular weight between 300 and 3000 Da as energy acceptors.

Interaction in the sense of the invention means changes in the distance between biomolecules that can be detected by FRET measurement. In order to detect this interaction, it is necessary that a FRET donor as well as a FRET acceptor are coupled to a biomolecule or each is coupled to one partner of a binding pair and that the interaction leads to a change in the distance between the donor and acceptor.

In a preferred embodiment one partner of a bioaffine binding pair is labelled with the donor and the other is labelled with the acceptor. The donor and acceptor come into very close proximity as a result of the formation of the binding complex between the partners of the bioaffine binding pair and FRET becomes possible.

Known examples of bioaffine binding pairs are in particular complementary nucleic acid sequences (DNA, RNA or peptidic nucleic acids), ligands and receptors, antigen or hapten and antibodies, or lectins and sugars. Under suitable conditions the partners of these binding pairs associate to form complexes.

The extent of complex formation is preferably used to determine the concentration of an analyte molecule. For this purpose the reaction conditions are selected in a manner known to a person skilled in the art such that depending on the test format either an increase or decrease in the signal occurs which depends on the analyte concentration.

Another preferred embodiment of an interaction in the sense of the invention is when the donor and acceptor are originally present under conditions which allow FRET but the FRET is interrupted for example by enzymatic activity between the donor and acceptor coupling site Fluorescence energy transfer is understood as the transfer of energy from a donor dye to an acceptor dye during which the donor emits the smallest possible amount of measurable fluorescent energy. In this method a fluorescent dye donor is for example excited with light of a suitable wavelength. Due to its spatial vicinity to a suitable second dye, the acceptor, this results in a so-called non-radiative i.e. radiation-free energy transfer to the acceptor (Van der Meer, et al., Resonance Energy Transfer VCH (1994)). If the second dye is a fluorophore or luminophore, the light emitted by this molecule at a particular wavelength can be used for a qualitative as well as for a quantitative determination.

In many test systems based on this FRET principle the luminophore group acting as a donor is excited and converted by absorption of a photon from a ground state into an excited state. If the excited donor molecule is close enough to a suitable acceptor molecule, the excited state can be transferred from the donor to the acceptor. This energy transfer results in a decrease in the fluorescence or luminescence of the donor and, if the acceptor is itself luminescent, results in an increased luminescence. If the acceptor is a quencher, it of course exhibits no fluorescence.

The efficiency of the energy transfer depends very strongly on the distance between the donor and the acceptor molecule. The decrease in signal depends on the sixth power of the separation distance. Due to this dramatic effect of the distance between the donor and acceptor, FRET pairs (also referred to as FRET systems) can be used to examine how many donor and acceptor molecules are present in close proximity to one another. This property is used for example to determine the presence of an analyte by contacting it with a specific partner. Numerous applications of FRET systems are known from the prior art. For this reference is in particular made to WO 00/47693, EP 76 695; Hemmilä, Chermcal Analysis 117, John Wiley & Sons, Inc. (1991) 135–139; and Van der Meer et al., Resonance Energy Transfer VCH (1994) supra.

Preferred embodiments of FRET systems are detection methods which additionally utilize a time-delayed measurement of the signal from a FRET system. Basic devices and methods for determining time-resolved FRET signals are described in the prior art. The principle of time-resolved FRET measurements is essentially based on selecting a measuring window such that interfering background fluorescence that may for example be due to interfering substances in the sample, is not co-detected, but rather only the fluorescence generated or suppressed by the energy transfer is measured.

The resulting fluorescence of the TR-FRET system is determined by means of appropriate measuring devices.

Such time-resolved detection systems use for example pulsed laser diodes, light emitting diodes (LEDs) or pulsed dye lasers as the excitation light source. The measurement occurs after an appropriate time delay i.e. after the interfering background signals have decayed. The basic design of such measuring equipment is shown in FIG. 1. Commercially available measuring systems e.g. based on Xenon flash lights such as Victor™ from Wallac Oy, are not suitable for the sensitive determination of time-delayed fluorescence in the range of a few $\mu$s as is required for FRET-pairs according to the invention but only for FRET systems having a lifetime of more than 10 $\mu$s.

The detection can preferably also be carried out using a phase modulation technique In this case the intensity of the excitation light is modulated with a high frequency and likewise the intensity of the emission also. The lifetime results in a phase shift and demodulation of the fluorescence emission. Explicit reference is herewith made to relevant information on the corresponding systems (WO 00/47693; French et al., SPIE BiOS in Proc. SPIE v 3259 (1998) 209–218 and French, et al., SPIE BiOS in Proc. SPIE v 3603 (1999) 272–280). A person skilled in the art will find the necessary information in these references to successfully use the dye combinations according to the invention also in such fluorescence modulation systems. The following mainly relates only to TR-FRET but it is obvious to a person skilled in the art that he can also use the phase modulation technique to measure the FRET pairs according to the invention.

FRET systems based on metallic complexes as energy donors and dyes from the class of phycobiliproteins as energy acceptors are known in the prior art (EP 76 695; Hemmilä, Chemical Analysis 117, John Wiley & Sons, Inc., (1991) 135–139). Established commercial systems (e.g. from Wallac, OY or Cis Bio Packard) use a FRET pair consisting of a lanthanide chelate as the metallic complex and a phycobiliprotein.

The advantageous properties of the lanthanide-chelate complexes in particular of europium or terbium complexes are known and can be used in combination with quenchers as well as in combination with fluorophores. The combination of such lanthanide-chelate complexes with low molecular fluorophores does not appear to result in a substantial improvement in the sensitivity (U.S. Pat. No. 5,998,146 and Blomberg et al., supra).

Ruthenium complexes per se are used as fluorophores or luminophores especially for electro-chemoluminescence. Preferred ruthenium-chelate complexes are for example known from EP 178 450 and EP 772 616 in which preferred methods for coupling these complexes to biomolecules are also described. Their use as energy donors in FRET systems is not discussed there.

Allophycocyanins have excellent properties such as unusually high extinction coefficients (about 700 000 L/M cm) and also extremely high emission coefficients. These are ideal prerequisites for their use as fluorophore acceptors in FRET systems. Moreover these dyes are known to be readily soluble in water and stable.

The term low molecular fluorophore refers to fluorophoric dyes having a molecular weight between 300 and 3000 Da. Such low molecular fluorophoric groups such as xanthenes, cyanins, rhodamines and oxazines have considerable disadvantages compared to the APCs with regard to important characteristics. Thus for example their extinction coefficients are substantially lower and are in the range of ca. 100 000 L/M cm. It is also known that unspecific binding due to the hydrophobic properties of these chromophores is a potential disadvantage for these dyes as acceptors in FRET systems.

It has now been surprisingly found that the FRET pairs according to the invention consisting of a metal chelate complex containing metal ions from the VIIth and VIIIth group of the transition elements, preferably rhenium, osmium, iridium or ruthenium, particularly preferably ruthenium, on the one hand, and a low molecular fluorophore on the other hand, have major advantages in FRET measurements especially with regard to sensitivity.

Surprisingly it was found that the dye combinations described in this invention lead to very sensitive test systems and even to an improvement of the lower limit of detection e.g. in measurement procedures based on the principle of time-delayed measurement in FRET systems.

It was also found that those dyes from the abovementioned dye classes which have an absorption maximum at a wavelength between 600 nm and 750 nm are particularly suitable. Consequently a preferred embodiment of the present invention is a method for determining the interaction between biomolecules labelled with a donor or acceptor based on the principle of fluorescence energy transfer and for example the time-delayed measurement of the resulting fluorescence which is characterized by the combined use of metal chelate complexes as described above and low molecular fluorophores having an absorption maximum between 600 nm and 750 nm.

If a ruthenium complex such as that described in EP 178 450 or EP 772 616 is used as a donor in a FRET system, a particularly suitable acceptor molecule should have an absorption maximum at wavelengths between 600 nm and 750 nm and especially preferably in the wavelength range between 630 nm and 700 nm.

In a particularly preferred embodiment of the invention the low molecular fluorophore molecule is further characterized in that it has a molecular weight of less than 2000 Da or preferably less than 1500 Da or particularly preferably less than 1000 Da. In this context the molecular weight of e.g. 1000 Da relates to the dye component per se i.e. not to additional linker structures or other coupling products. The low molecular fluorophore preferably has a molecular weight of at least 300 Da and preferably of at least. 350 Da.

Dyes from the following classes of substances have proven to be particularly suitable: xanthenes, cyanins, rhodamines and oxazines. Hence in a particularly preferred embodiment of the invention the low molecular fluorophoric dye is selected from a group comprising xanthenes, cyanins, rhodamines and oxazines.

Dyes from the rhodamine group are described in detail in EP 567 622. This application also describes which measures can be used to obtain rhodamine dyes whose absorption maximum is shifted towards light of longer wavelengths. Fluorophores from the class of rhodamines of the following general formula (formula I) are particularly preferred as low molecular fluorophores.

Formula I: Rhodamines

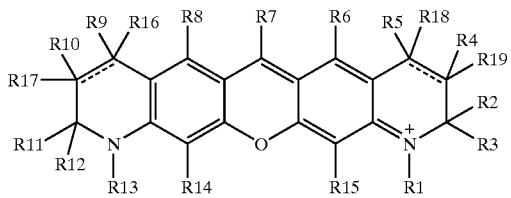

in which R1 and R13 are the same or different and denote: hydrogen, alkyl with 1 to 20 carbon atoms, polyoxyhydrocarbyl units, phenyl, phenylalkyl with 1 to 3 carbon atoms in the alkyl chain wherein the alkyl or/and phenyl residues can be substituted by one or more hydroxy, halogen, sulphor, carboxy or alkoxycarbonyl groups in which alkoxy can have 1 to 4 carbon atoms; R7 denotes an alkyl group substituted by at least one halogen with 1 to 20, preferably 1 to 7 carbon atoms or a phenyl group which is substituted by a carboxy or alkoxycarbonyl group in the o-position relative to the carbon atom bound to the pentacyclic ring system and by at least one halogen and wherein alkoxy can have 1 to 4 carbon atoms, or a carboxyalkyl group or a carboxymethyleneoxyalkyloxy group;

the two bonds marked by the dashed lines mean that the two carbon atoms linked by the dashed bond can be linked together by a single or double bond; wherein R14, R15 and the other positions of the pentacyclic basic structure that are not labelled with specific symbols can be substituted by alkyl groups with 1 to 20 carbon atoms; wherein X is a counterion and wherein at least one of the residues R1, R7 or/and R13 is coupled to a biomolecule.

Those rhodamines are especially preferred in which the residue R7 is a strong electron-attracting group. Such electron-attracting groups on R7 are preferably polyhalogencarboxyphenyl and perfluoroalkyl residues. Tetrachlorocarboxyphenyl residues and polyhalogenphenyl residues are especially preferred at position R7. These exhibit a particularly good stability over a broad pH range. The fine tuning of the wavelength of the rhodamine dyes can be achieved by introducing double bonds and additionally by methyl substituents on the residues R2, 3, 11, 12, 5 and/or 9. They are preferably linked to biomolecules via the residues R1 or R13. In addition the linker lengths can also be optimized for test performance.

The hydrophilicity of such pentacyclic rhodamine dyes can also be modified over a wide range by substitution with appropriate-hydrophilic groups. Sulfonic acid groups are preferably used which can in principle be introduced at any positions. If the sulfonic acid group is introduced at one of the positions R1 and R13, the other position is then preferably substituted with carboxyalkyl.

In a further preferred embodiment oxazines of the following general formula are used as fluorescence resonance energy acceptors.

Formula II: Oxazines

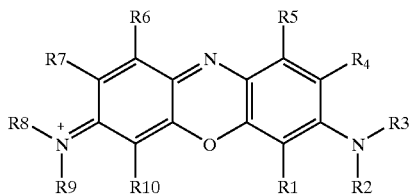

in which R1, R4, R5, R6, R7, R10 denote hydrogen, alkyl, hydroxy, halogen, carboxyl, sulfonyl or amino and R2, R3 denote hydrogen, alkyl, alkoxy, polyoxyhydroxycarbonyl units, phenyl, phenylalkyl which can be substituted by hydroxy, sulfonyl, carboxy, amino, alkoxycarbonyl, and in which R2 and R1 or R3 and R4 can form a saturated or unsaturated C4 or C5 bridge and R8, R9 denote hydrogen, alkyl, alkoxy, polyoxyhydroxycarbonyl units, phenyl or phenylalkyl which can be substituted by hydroxy, sulfonyl, carboxy, amino, alkoxycarbonyl, in which R2 and R1 or R3 and R4 can form a saturated or unsaturated C4 or C5 bridge and wherein at least one of the residues R2, R3, R8 or R9 represents a non-bridge forming residue that is coupled to a biomolecule and wherein at least one of the residues R2, R3, R8 and R9 represents a bridge-forming residue which can be optionally substituted by alkyl.

Oxazines and their coupling to biomolecules are described in EP 747 447. Reference is herewith made to its description of oxazine dyes and the preferred embodiments. Oxazine dyes in which R3, R4 and/or R7, R8 can form a ring structure are particularly preferred since this results in a substantial improvement in the quantum yield. The absorption wavelength and the hydrophilicity can be fine tuned as described above for rhodamines.

Other preferred dyes are selected from the classes of cyanins (see Mujumdar et al., Bioconjugate Chem. 7, 1996, 356–362) or xanthenes (EP 1 054 039).

A large number of test configurations for determining the achievable sensitivity of a FRET pair to be examined, are conceivable and feasible depending on the test, analyte and binding or detection reagent. However, such systems obviously lack comparability with one another and transferability to other systems.

It is expedient to use the biotin-streptavidin system as a standard system for determining the lower limit of detection (LLD). The low molecular biotin is bound very strongly by streptavidin. This high affinity binding pair enables a reproducible comparative determination of the sensitivities that can be achieved by different FRET pairs.

It is preferable to use the biotin-streptavidin system to determine the lower limit of detection for a FRET pair to be examined. For this the FRET energy donor complex is bound to streptavidin as described in example 1b). The low molecular acceptor dye is coupled to biotin using diaminodioxa-octane (DADOO) as a linker (cf examples 1d) and 1e)). The sensitivity is preferably determined as described in example 3.

The procedure described above can be used to select FRET pairs according to the invention in such a manner that the lower limit of detection is improved. Those FRET pairs are preferred which are composed of metal ions of the VIIth and VIIIth group of the transition elements as donors and low molecular acceptors which have a lower limit of detection of $3.0 \times 10^{-13}$M under the conditions defined above. Preferred FRET pairs have a lower limit of detection of $2 \times 10^{-13}$M, particularly preferred FRET pairs have a lower limit of detection of $1 \times 10^{-13}$M.

Hence the invention also concerns an improved method for determining the interaction between biomolecules labelled with a donor or acceptor based on the principle of fluorescence resonance energy transfer and measurement of the resulting fluorescence characterized in that metallic chelate complexes containing metal ions of groups VII and VIII of the transition elements are used as energy donors in combination with low molecular fluorophores having a molecular weight between 300 Da and 3000 Da as energy acceptors.

A preferred embodiment of the invention concerns a homogeneous test with improved sensitivity for determining the interaction between biomolecules labelled with a donor or acceptor based on the principle of fluorescence resonance energy transfer and measurement of the resulting fluorescence characterized in that metallic chelate complexes containing metal ions of groups VII and VIII of the transition elements are used as energy donors in combination with low molecular fluorophores having a molecular weight between 300 Da and 3000 Da as energy acceptors.

A person skilled in the art can very easily select optimal combinations of donor and acceptor for his purposes based on the present invention.

The novel sensitive FRET pairs according to the invention are particularly preferably used to determine molecular interactions. Examples of such interactions are in particular hybridizing reactions of nucleic acids, binding of biomolecules to corresponding receptors and interactions between antigen or hapten and antibody, or other bioaffine binding pairs e.g. between lectin and sugar.

However, FRET pairs can also be used to for example measure the distance between the donor and acceptor molecule. Changes in the distances between such molecules can for example be used to document an enzymatic activity. The use of metallic chelate complexes as energy donors in combination with low molecular fluorophores as energy acceptors to determine interactions between biomolecules is therefore also a particularly preferred embodiment of this invention.

A particular advantage of ruthenium complexes is their lifetime in the range of 50 ns–ca. 10 μs which allows a high repetition rate as well as a short dead time in the measurement. Lifetime is understood as the time which elapses until half of the energy of a FRET system has been radiated. The short lifetime of the dye pairs according to the invention using ruthenium complexes as donors is particularly advantageous because repetitive, i.e. multiple, measurements can be carried out. If for example europium chelate complexes are used as donors it is usual to select a measuring window in a time range of ca. 300 μs to 1 ms and it is usual to measure over a time period of ca. 200 μs. This procedure is due to the long lifetime of the excited europium complexes which would make shorter measuring windows disadvantageous. In contrast the dye pairs according to the invention, for example using ruthenium complexes as donors, have major advantages. The ruthenium complexes usually have a lifetime of ca. 50 ns–10 μs. Since the low molecular fluorophores have very short lifetimes, the lifetime of the metal chelate complex is decisive for the optimal time window for measuring the FRET pairs according to the invention. An individual measuring cycle can be completed within ca. 100 μs or less and the measuring cycles can be repeated several times. This leads to a considerable improvement in sensitivity. FRET dye pairs using ruthenium complexes as donors which have lifetimes of 50 ns to 10 μs are therefore particularly preferred. Pairs having a lifetime of 100 ns to 8 μs have proven to be especially preferred.

The FRET pairs according to the invention are preferably used to for example determine the presence or concentration of a biomolecule. In this case it is particularly preferred that one partner of the FRET pair is bound to a binding partner for the said biomolecule while another partner of the FRET pair is bound or becomes bound directly or indirectly to the said biomolecule. A simple system of this kind for example uses antigen labelled with metal chelate and fluorophore-labelled antibody (or vice versa). Corresponding models and examples are described in the method section.

As already mentioned a particular advantage of FRET systems and especially of TR-FRET systems is that interactions between biomolecules can be determined without washing steps i.e. in so-called homogeneous methods of determination. Hence homogeneous methods of determination using the dye combinations according to the invention are particularly preferred.

The two partners of the dye pairs according to the invention i.e. metal (transition elements of group VII or VIII)-chelate donor on the one hand and low molecular fluorophore on the other hand can be coupled in a known manner to biomolecules as described for example in EP 178 450 and EP 772 616 (hydrophilic metal complexes) or in EP 567 622 or EP 747 447. These coupling products are readily soluble in water and very stable under transport or storage conditions. Hence they are very well suited for preparing test or reagent kits which enable the detection of an analyte in a sample wherein at least one biomolecule labelled with a metal chelate complex and at least one other biomolecule that is labelled with a low molecular fluorophore are contained in this reagent kit.

A preferred embodiment of the invention is a reagent or a reagent combination for determining the interaction between the partners of a bioaffine binding pair characterized in that one partner of a bioaffine binding pair is labelled with a metal chelate complex containing metal ions from the VIIth and VIIIth group of the transition elements and another partner of this bioaffine binding pair is labelled with a low molecular fluorophore having a MW between 300 Da<3000 Da.

Another preferred embodiment of the invention is a reagent kit which, in addition to the biomolecules labelled with the FRET partners, also contains other useful reagents which are used to carry out the analyte determination, and are for example certain buffers and control reagents.

The following examples, the cited publications, the sequence protocol, the formulae and the figure further elucidate the invention whose protective scope is derived from the patent claims. The described methods are to be understood as examples which still describe the subject matter of the invention even after modification.

FIGURES

FIG. 1: Diagram of the measuring device

Schematic representation of the measuring apparatus used within the scope of the present invention for time-resolved fluorescence measurement. This measuring arrangement and its use is described and elucidated in more detail in the following examples.

EXAMPLES

Abbreviations Used

| | |
|---|---|
| DADOO = | 1,8 diamino-3,6-dioxaoctane |
| batho = | bathophenanthroline disulfonic acid |
| bpy = | 2,2'-bipyridyl-4-methyl-4'-butylcarboxylic acid |
| APC = | allophycocyanin |
| HA = | human haemagglutinin |
| HA peptide = | YPYDVPDYA |
| Osu = | O-succinimide |
| Strept. = | streptavidin |
| Ru = | ruthenium |
| Eu = | europium |

Example 1

Syntheses and Labelling of Biomolecules a) Synthesis of Ru(batho)$_2$bpy-Osu 50 mg ($3*10^{-5}$ mol) Ru(batho)$_2$bpy is dissolved in DMF, 12 mg ($6*10^{-5}$ mol) EDC (N-(3-dimethylaminopropyl)-N'-ethylcarbodiimide hydrochloride) and 7 mg ($6*10^{-5}$ mol) NHS (N-hydroxysuccinimide) are added and stirred overnight at room temperature. The reaction product is precipitated by adding acetone. The precipitate is separated by filtration and dried in a vacuum. It is purified by means of HPLC. The final product is analysed by means of MALDI-MS and corresponds to formula III.

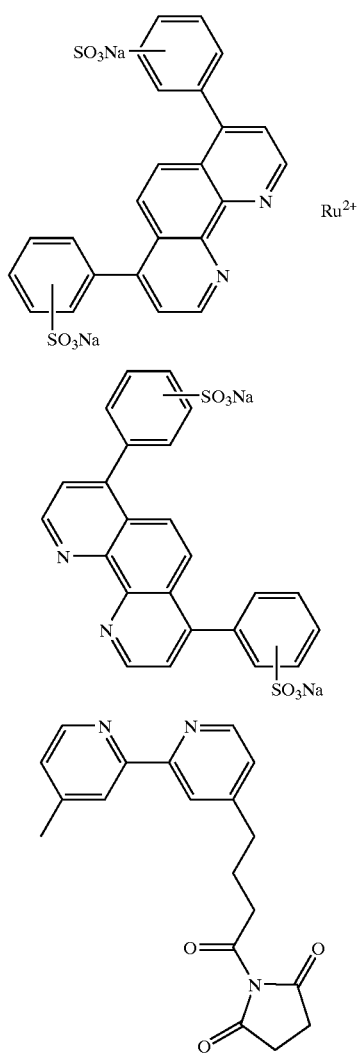

Formula III: Ru(batho)$_2$bpy-OSu b) Synthesis of Streptavidin-Ru(batho)$_2$pby 10 mg ($1.9*10^{-7}$ mol) streptavidin is dissolved in 1 ml N NaHCO$_3$ Solution and 2 mg ($1.3*10^{-6}$ mol) Ru(batho)$_2$bpyOSu (dissolved in 0.5 ml of an aqueous 0.1 N NaHCO$_3$ solution) is added dropwise. It is stirred for one hour at room temperature and the mixture is chromatographed on a Sephadex LH20 column (eluent 0.1 N NaHCO$_3$ solution). The product fractions, i.e. the fractions which contain the labelled streptavidin (protein O.D. 280 nm), are dialysed overnight against H$_2$O and subsequently freeze-dried.

The degree of labelling was determined by comparing the absorption at 280 nm (protein) and 460 nm (Ru$^{2+}$ complex) and determined as ca. 3.6 Ru$^{2+}$ complexes per streptavidin. Streptavidin-ruthenium conjugates having an average of 3 to 5 Ru$^{2+}$ complexes per streptavidin molecule are suitable for determining the sensitivity.

c) Coupling of Ru(batho)$_2$pby to MAB-anti HA 1 mg ($0.65*10^{-6}$ mol) Ru(batho)$_2$bpyOSu (dissolved in 1.0 ml of an aqueous 0.1 N NaHCO$_3$ solution) is added dropwise to 300 μl (3 mg) MAB-anti HA. It is stirred for one hour at room temperature and the mixture is chromatographed on an LH20 column (eluent 0.1 N NaHCO$_3$ solution). The product fractions, i.e. the fractions that contain the labelled antibody (O.D. 280 nm), are pooled and frozen as 0.1 N NaHCO$_3$ solutions.

In the present experiment an average of about 7 ruthenium complexes per antibody were bound.

d) Preparation of Biotin-JA286

10.2 mg ($3*10^{-5}$ mol) biotin-DADOO and 17.2 mg ($3*10^{-5}$ mol) JA 286 are dissolved in 1 ml DMF, 15 μl triethylamine is added and cooled to 0° C. After adding 5 μl DECP (diethyl cyanophosphonate), the mixture is stirred for 1 hour at 0° C. and subsequently overnight at room temperature. After evaporating to dryness the crude product is purified by means of HPLC. The final product was characterized by MALDI-MS and corresponds to formula IV:

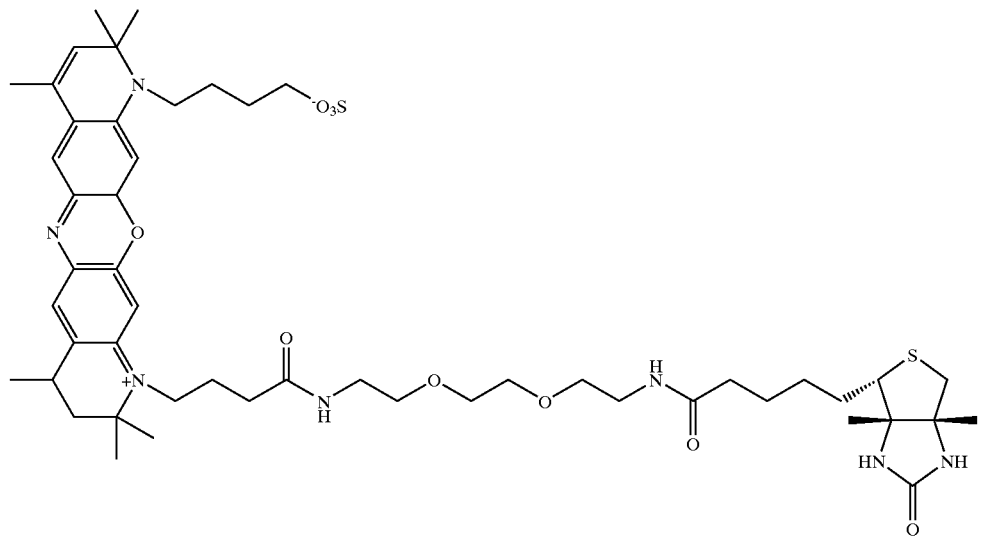

Formula IV: Biotin-JA286 e) Synthesis of Biotin-JA198

5 mg ($5.3*10^{-6}$ mol) JA198-OSu and 2 mg ($5.3*10^{-6}$ mol) biotin-DADOO are dissolved in 800 µl phosphate buffer pH 7.5 and stirred overnight at room temperature in the dark. Subsequently the mixture is purified by HPLC. The product was examined with ESI-MS and corresponds to formula V:

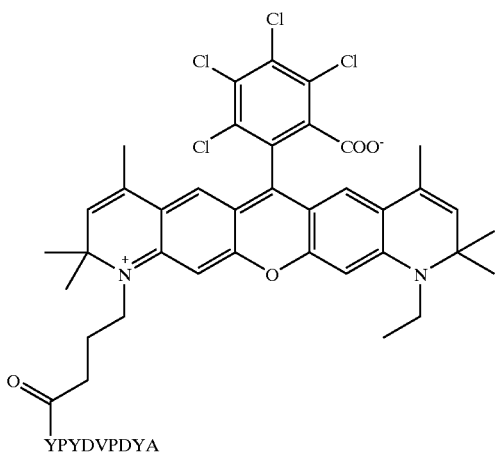

Formula V: Biotin-JA198 f) Coupling of JA133 to the Synthetic HA Peptide 5 mg ($4.5*10^6$ mol) HA peptide (YPYDVPDYA=SEQ ID NO: 1) is dissolved in 1 ml acetonitrile/phosphate buffer pH 7.5 (1:1) and a solution of 4 mg ($4.5*10^{-6}$ mol) JA133-OSu and 500 µl acetonitrile are added while stirring. The mixture is stirred overnight at room temperature.

After evaporating to dryness in a vacuum, it is purified by means of HPLC. The product was examined by means of ESI-MS and corresponds to formula VI:

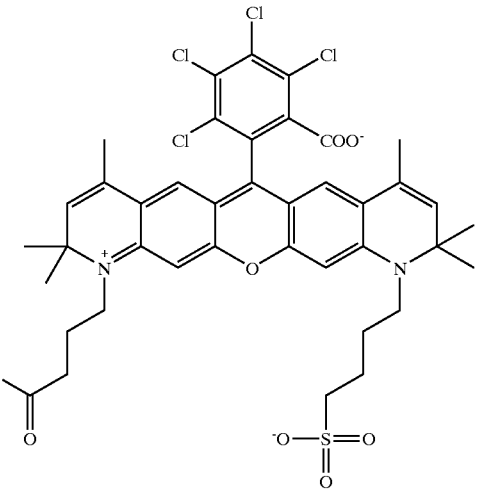

YPYDVPDYA

Formula VI: HA Peptide-JA133

Example 2

Measuring Device and Description Thereof

The measuring apparatus used in the present invention for time-resolved fluorescence measurement is described in the following and elucidated by a diagram (FIG. 1).

The pulsed light source (1)—nitrogen laser or dye laser—excites the donor marker of the measuring sample (3) with light pulses of a suitable wavelength (13), the width of the light pulse t=0.7 ns being much shorter than the decay time of one of the fluorescent markers. The acceptor marker is then excited to fluoresce by energy transfer. This fluorescence radiation (14) is guided with an optical system (4,6) through an optical filter (cut-off filter/band pass filter) (5) which allows the emission wavelength of the acceptor marker to pass, onto the photocathode of a photomultiplier (7). The individual detected photons generate current pulses which can be counted digitally (10) (photon counting method) after amplification (8) and standardization (9). A part of the excited light (15) is deflected by a quartz plate (2) to a photodiode (11) which controls a gate switch (12) which starts the counter (10) after a preset delay time of preferably 1 µs and stops the counting process again after an adjustable opening time of the measuring window which is preferably 100 µs. The delay time is selected such that scattered light effects and background fluorescence have almost completely decayed within this time. In this manner the number of counted current pulses is proportional to the intensity of the marker fluorescence which is measured separately from the background. The procedure for such measurements is described in detail in examples 3 and 4 for two new TR-FRET pairs. The other new FRET pairs described in example 5 are measured in a similar manner or the europium-APC systems of example 5 are quantified using known instruments and methods from the prior art.

Example 3

Procedure for Measuring the Sensitivity of a FRET System Comprising a $Ru^{2+}$ Complex as the Donor and JA-286 as the Fluorophoric Acceptor 400 µl of a solution (10 mM Na phosphate, 150 mM NaCl, pH 7.2) containing 100 nM streptavidin labelled with the $Ru^{2+}$ complex and 300 nM biotin-DADOO-JA-286 is pipetted into a measuring cuvette.

The measurement is carried out with the apparatus described in example 2 and shown schematically in FIG. 1. The donor is excited by a 460 nm dye laser. The light pulse duration is 1 ns. The fluorescence of the system is detected by a combination of an optical cut-off filter KV550+RG645 and the photomultiplier according to the described experimental arrangement using the photon counting technique.

The delay time is set to 1 μs and the measuring window is 100 μs. The background is determined by a separate measurement of the buffer under the same conditions. The sensitivity (lower limit of detection) is given by a limiting concentration which is determined by the following relationship:

$$C_0 = \frac{2B}{S}C_s,$$

in which $C_0$ is the limiting concentration in [M], B is the background in [counts], S is the signal in [counts] and CS is the sample concentration in [M].

The lower limit of detection of this system is $7.4 \cdot 10^{-14}$ M streptavidin.

Example 4

Procedure for Measuring the Sensitivity of a FRET System Comprising $Ru^{2+}$ Complex as the Donor and JA-133 as an Acceptor in an Antigen-Antibody Reaction The FRET partners in this example are the $Ri^{2+}$ complex from example 1a) as the donor and JA-133 as the acceptor. A monoclonal antibody to HA is labelled with the donor as described under 1c). The antigen (HA peptide) is labelled with the acceptor according to 1f). The donor-acceptor pair are brought sufficiently closely to one another by the antigen-antibody reaction such that FRET is possible and measurable.

After 10 minutes incubation at room temperature, 400 μl of a solution (10 mM Na phosphate, 150 mM NaCl, pH 7.2) containing 100 nM anti-HA labelled with the $Ri^{2+}$ complex and 100 nM HA-JA-133 is pipetted into the measuring cuvette.

The measurement is carried out with the apparatus described in example 2. The donor is excited at 460 nm by a 460 nm dye laser. The light pulse duration is 1 ns. The fluorescence of the system is detected by a combination of an optical cut-off filter KV550+RG630 and the photomultiplier according to the described experimental arrangement using the photon counting technique.

The delay time is set to 1 μs and the measuring window is 100 μs. The background is determined by a separate measurement of the buffer under the same conditions. The sensitivity is given by a limiting concentration $C_0$ in [mol/liter] as stated in example 1. The sensitivity of this system is $7.2 \cdot 10^{-14}$ M HA.

Example 5

Combination of Some New FRET Pairs and Comparison with FRET Pairs from the Prior Art a) TR-FRET pair 1: Streptavidin-Bu(batho)$_2$bpy/biotin-APC The labelled streptavidin from example 1b) was used at a concentration of 100 nM and APC biotin (commercial product: APC-XL biotin from Europa Bioproducts Ltd., Cambridge, GB) was used at a concentration of 300 nM. The excitation wavelength ($\lambda_{EX}$) was at 460 nm and the emission or measuring wavelength ($\lambda_{EM}$) was at 634 nm. A lower limit of detection of $4.1 \times 10^{-13}$ mol/liter (=M) was determined with this dye and reagent pair.

b) R-FRET Pair 2: Streptavidin-Ru(batho)2bpy/biotin-JA198

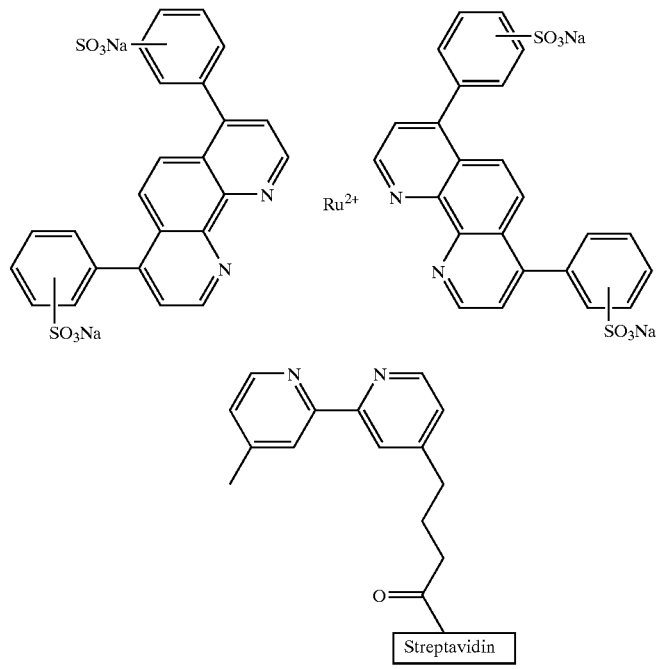

-continued
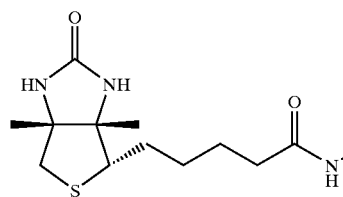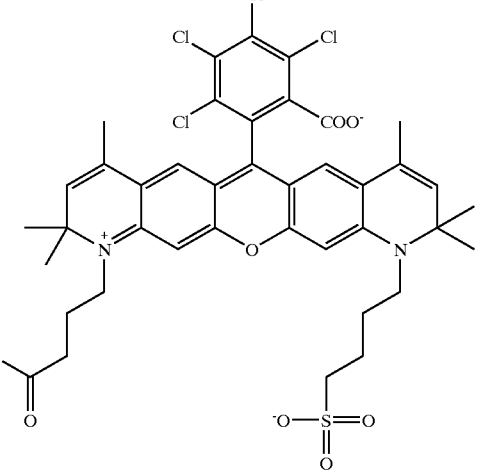
c) TR-FRET Pair 3: Streptavidin-Ru(batho)2bpy/biotin-JA286
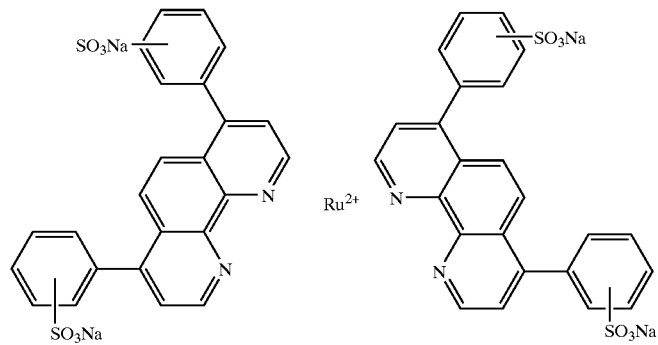
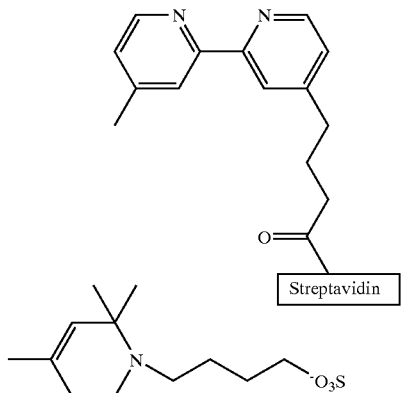
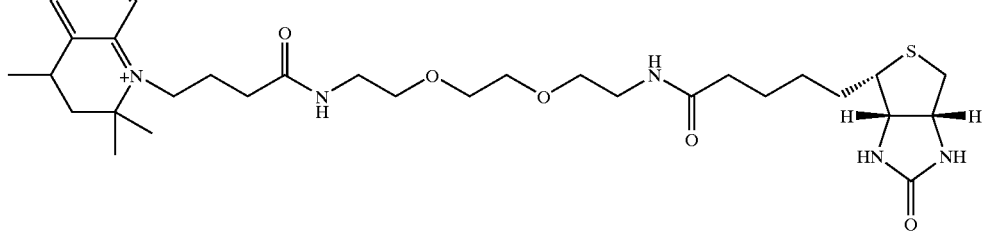

d) TR-FRET Pair 4: MAB-anti-HA-Ru(batho)2bpy/HA-JA133

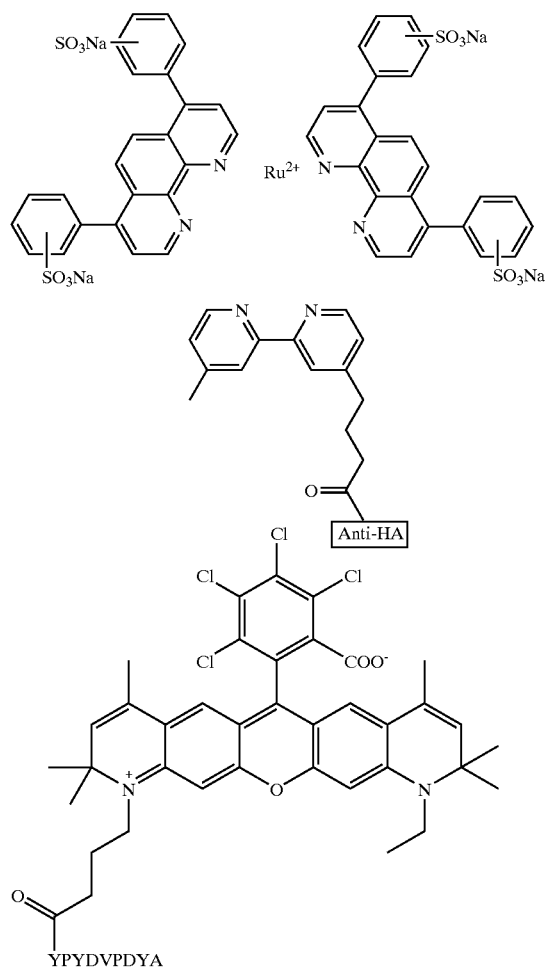

e)+f) Additional FRET Pairs using Commercially Available Raw Materials.

Commercially available streptavidin derivatives labelled with europium from Wallac, Oy (Strept-Eu0062: AD0062 streptavidin-W1024; Strept-Eu0060: AD0060 streptavidin-W8044) were used for the FRET pairs 5 and 6 in table 1. Commercially available-biotin-APC described in example 5a) was used as the acceptor.

The sensitivity was measured as follows:

1 $\mu$s delay and 100 $\mu$s measuring window determined according to $$C_0 = \frac{2B}{S} C_s, [M],$$

in which $C_0$ is the limiting concentration in [M], $C_s$ is the concentration used in [M], B is the background (of the buffer) in [counts] and S is the signal in [counts].

(#): Measuring Window: 400 $\mu$s—As Described in the Prior Art for Eu-APC Complexes.

Table 1 clearly shows that the novel FRET pairs are at least equivalent to or superior to the known systems in the prior art. The FRET pair No. 3 according to the invention has an LLD of $7.4 \cdot 10^{-14}$ which is considerably lower than the LLD for examples No 5 or No 6 according to the prior art.

List of References

EP 178 450
EP 567 622
EP 747 447
EP 076 695
EP 772 616
EP 439 036
EP 1 054 039
U.S. Pat. No. 5,998,146
WO 00/47693

Blomberg, et al., Clinical Chemistry 45 (1999) 855 ff.
French, et al., SPIE BiOS in Proc. SPIE v 3259 (1998) 209–218
French, et al., SPIE BiOS in Proc. SPIE v 3606 (1999) 272–280
Hemmilä, Chemical Analysis 117
John Wiley & Sons, Inc., (1991) 135–139
joun et al., Analytical Biochemistry 232 (1995) 24–30
Mujumdar, et al., Bioconjugate Chem. 7, 1996, 356–362
Van der Meer, et al., Resonance Energy Transfer VCH (1994)

TABLE 1

Lower limit of detection for some examined FRET pairs

| No. | System | Concentration [$\mu$M] strept./biotin | $\lambda_{F,X}$ [nm] | $\lambda_{F,M}$ [nm] | Lower limit of detection (LLD) [mol/litre] |
|---|---|---|---|---|---|
| 1 | strept.-Ru(batho)$_2$bpy/biotin-APC | 0.100/0.300 | 460 | 346 | $4.1 \cdot 10^{-13}$ |
| 2 | strept.-Ru(batho)$_2$bpy/biotin-JA198 | 0.150/0.150 | 460 | 660 | $2.6 \cdot 10^{-13}$ |
| 3 | strept.-Ru(batho)$_2$bpy/biotin-JA286 | 0.100/0.300 | 460 | 703 | $7.4 \cdot 10^{-14}$ |
| 4 | anti-HA-Ru-(batho)$_2$bpy/HA-JA133 | 0.100/0.100 | 460 | 631 | $7.2 \cdot 10^{-14}$ |
| 5(#) | strept.-Eu0062/biotin-APC | 0.030/0.090 | 337 | 660 | $2.5 \cdot 10^{-11}$ |
| 6(#) | strept.-Eu0060/biotin-APC | 0.030/0.090 | 337 | 660 | $7.3 \cdot 10^{-12}$ |

What is claimed is:

1. Method for determining an interaction between biomolecules labelled with a donor or acceptor, respectively, based on fluorescence resonance energy transfer and measurement of resulting fluorescence wherein metallic chelate complexes containing metal ions from groups VII and VIII of transition elements are used as energy donors in combination with low molecular fluorophores having a molecular weight between 309 Da and 3000 Da as energy acceptors.

2. Method as claimed in claim 1, wherein the lower molecular fluorophores have an absorption maximum between 600 nm and 750 nm.

3. Method as claimed in claim 1, wherein the low molecular fluorophores have a molecular weight of <2000 Da.

4. Method as claimed claim 1, wherein the fluorophores are selected from the group consisting of xanthenes, cyanins, rhodamines and oxazines.

5. Method as claimed in claim 1, wherein a rhodamine of general formula I is used as the fluorophore

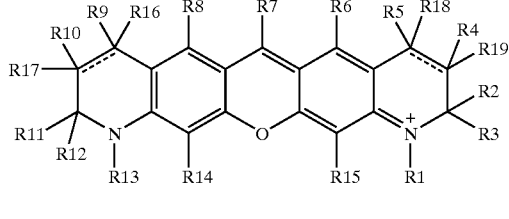

(formula 1)

X− in which R1 and R13 are the same or different and denote: hydrogen, alkyl with 1 to 20 carbon atoms, polyoxyhydrocarbyl units, phenyl, phenylalkyl with 1 to 3 carbon atoms in the alkyl chain wherein the alkyl or/and phenyl residues can be substituted by one or more hydroxy, halogen, sulpho, carboxy or alkoxycarbonyl groups in which alkoxy can have 1 to 4 carbon atoms;

R7 denotes an alkyl group substituted by at least one halogen with 1 to 20, preferably 1 to 7 carbon atoms or a phenyl group which is substituted by a carboxy or alkoxycarbonyl group in the o-position relative to the carbon atom bound to the pentacyclic ring system and by at least one halogen and wherein alkoxy can have 1 to 4 carbon atoms, or a carboxyalkyl group or a carboxymethyleneoxy-alkyloxy group;

the two bonds marked by the dashed lines mean that the two carbon atoms linked by the dashed bond can be linked together by a single or double bond;

wherein R14, R15 and the other positions of the pentacyclic basic structure that are not labelled with specific symbols can be substituted by alkyl groups with 1 to 20 carbon atoms; wherein X is a counterion and wherein at least one of the residues R1, R7 or/and R13 is coupled to a biomolecule.

6. Method as claimed in claim 5, wherein the substituent R7 is an electron-attracting residue.

7. Method as claimed in claim 1, wherein an oxazine of general formula II is used as the fluorophore

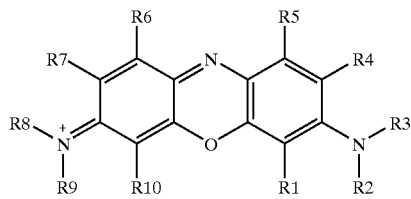

(formula II)

in which R1, R4, R5, R6, R7, R10 denote hydrogen, alkyl, hydroxy, halogen, carboxyl, sulfonyl or amino and R2, R3 denote hydrogen, alkyl, alkoxy, polyoxyhydroxycarbonyl units, phenyl, phenylalkyl which can be substituted by hydroxy, sulfonyl, carboxy, amino, alkoxycarbonyl, in which R2 and R1 or R3 and R4 can form a saturated or unsaturated C4 or C5 bridge and R8, R9 denote hydrogen, alkyl, alkoxy, polyoxyhydroxycarbonyl units, phenyl, phenylalkyl which can be substituted by hydroxy, sulfonyl, carboxy, amino, alkoxycarbonyl, in which R2 and R1 or R3 and R4 can form a saturated or unsaturated C4 or C5 bridge and wherein at least one of the residues R2, R3, R8 or R9 represents a non-bridge-forming residue that is coupled to a biomolecule and wherein at least one of the residues R2, R3, R8 and R9 represents a bridge-forming residue which can be optionally substituted by alkyl.

8. Method as claimed in claim 1, wherein the metal chelate complex is a ruthenium complex.

9. Method as claimed in claim 1, wherein a time-resolved measurement of fluorescence is carried out.

10. Method as claimed in claim 1, wherein the fluorescence is measured by a phase modulation technique.

11. Reagent kit for detecting an analyte in a sample, comprising at least one biomolecule labelled with a metal chelate complex containing metal ions from groups VII and VIII of transition elements and at least one further biomolecule which is labelled with a low molecular fluorophore.

12. Reagent combination for determining interaction between partners of a bioaffine binding pair, comprising one partner of a bioaffine binding pair that is labelled with a metal chelate complex containing metal ions from groups VII and VIII of transition elements and another partner of a bioaffine binding pair is labelled with a lower molecular fluorophore having a MW between 300 Da and 3000 Da.

* * * * *